United States Patent [19]

Greite

[11] Patent Number: 5,015,254
[45] Date of Patent: May 14, 1991

[54] INTRAOCULAR POSTERIOR CHAMBER LENS

[75] Inventor: Jürgen-Hinrich Greite, Munich, Fed. Rep. of Germany

[73] Assignee: Adatomed Pharmazeutische und Medizintechnische Gesellschaft MBH, Munich, Fed. Rep. of Germany

[21] Appl. No.: 416,673

[22] Filed: Oct. 5, 1989

[30] Foreign Application Priority Data

Aug. 18, 1989 [DE] Fed. Rep. of Germany ....... 3927360

[51] Int. Cl.⁵ .............................................. A61F 2/16
[52] U.S. Cl. ........................................................ 623/6
[58] Field of Search ............................................. 623/6

[56] References Cited

U.S. PATENT DOCUMENTS

| Re. 32,525 | 5/1989 | Pannu | 623/6 |
| 4,842,602 | 6/1989 | Nguyen | 623/6 |
| 4,880,427 | 11/1989 | Anis | 623/6 |

FOREIGN PATENT DOCUMENTS

| 0161765 | 11/1985 | European Pat. Off. | |
| 0246216 | 11/1987 | European Pat. Off. | 623/6 |
| 2581535 | 11/1986 | France | 623/6 |
| 2584919 | 1/1987 | France | 623/6 |

OTHER PUBLICATIONS

"The Jaffe Single Piece Posterior Chamber Lens from Cilco", Advertisement Brochure by Cilco, Oct. 1984, 2 pp. 623–626.

Primary Examiner—Ronald Frinks
Attorney, Agent, or Firm—Fleit, Jacobson, Cohn, Price, Holman & Stern

[57] ABSTRACT

Intraocular posterior chamber lens for implantation in the capsular sack of the human eye, in which fixation loops which extend semicircularly are atttached to a circular lens body so as to form a single piece with the lens body, the outer circumference of which fixation loops are designed to accomodate the equator of the capsular sack, thereby assuring a stress-free implantation despite radial stretching of the haptic.

8 Claims, 1 Drawing Sheet

INTRAOCULAR POSTERIOR CHAMBER LENS

DESCRIPTION

The invention relates to an intraocular posterior chamber lens for implantation in the capsular sack of the human eye.

In intraocular lenses known to the prior art, particularly posterior chamber lenses in which the lens is positioned in the eye by means of fixation loops, the capsular sack of the eye is highly deformed in the equatorial area during intraocular implantation. This is due to the fact that intraoclar lenses as they now exist are adapted in their overall diameter, not to the anatomical conditions of the capsular sack, but to those of the sulcus ciliaris (transition from iris to ciliary body). This results in a considerable ovoid distention of the capsular sack, which brings with it the danger both that the loops of the intraocular lens will pierce the capsular sack and bore into the ciliary body, which could result in serious tears, and that the lens will be displaced from the capsular sack, resulting in a reduction of the optical capacity and often necessitating the removal of the lens. In addition, the forward exposed capsular membranes may be drawn backwards due to the increased pressure or excessive strain exerted by the intraocular lens, so that there is no longer a mechanical barrier to the proliferation of cells in the equatorial area, with the result that secondary cataract formation is promoted.

The goal of the invention, therefore, is to create an intraocular posterior chamber lens for implantation in the capsular sack of the human eye, which can be implanted in the capsular sack without strain and which thereby approximates the physiological conditions of the natural lens of the eye.

This goal is achieved in the invention by the characterizing features of claim 1. In an advantageous manner, the invention permits the creation of a lens with a lens body that has a large cross-sectional surface and that can be fixed in the capsular sack without strain. The lens can be advantageously designed in such a way that attached to the circular optical lens body and forming a single piece with the lens body are two approximately semicircular fixation loops which extend tangentially and in identical circumferential direction from attachment points at diametrically opposite positions on the circumference of the lens body, with an increasing distance between either fixation loop and the circumference of the lens body as the loop extends from the point of attachment to its loose end.

In particular the semicircular fixation loops are adapted to the equator of the capsular sack, in which the lens is implanted. Most of all the inventive intraocular lens permits the outer circumference of the fixation loops to be reduced during implantation to the circumference of the lens body, which is preferably about 7 mm, thereby assuring a relatively small size for the opening that is to be provided for implantation of the lens on the front side of the capsular sack. After insertion of the lens in the capsular sack, the fixation loops more or less reassume their former positions and adjust themselves to the equator of the capsular sack. They then rest over their entire circumference on the equator of the capsular sack and do so without exerting strain. Swellings in the equatorial area of the capsular sack are thereby avoided. Since the opening in the front side of the capsular sack can be relatively small, there is no danger that the lens will fall out of the capsular sack. Despite the radial spread of the fixation loops, a stress-free implantation of the lens in the capsular sack is achieved, since the outer circumference of the fixation loops adjusts itself to the equator of the capsular sack.

The invention is described in greater detail on the basis of the attached diagrams, which show an invention embodiment.

Figure 1:
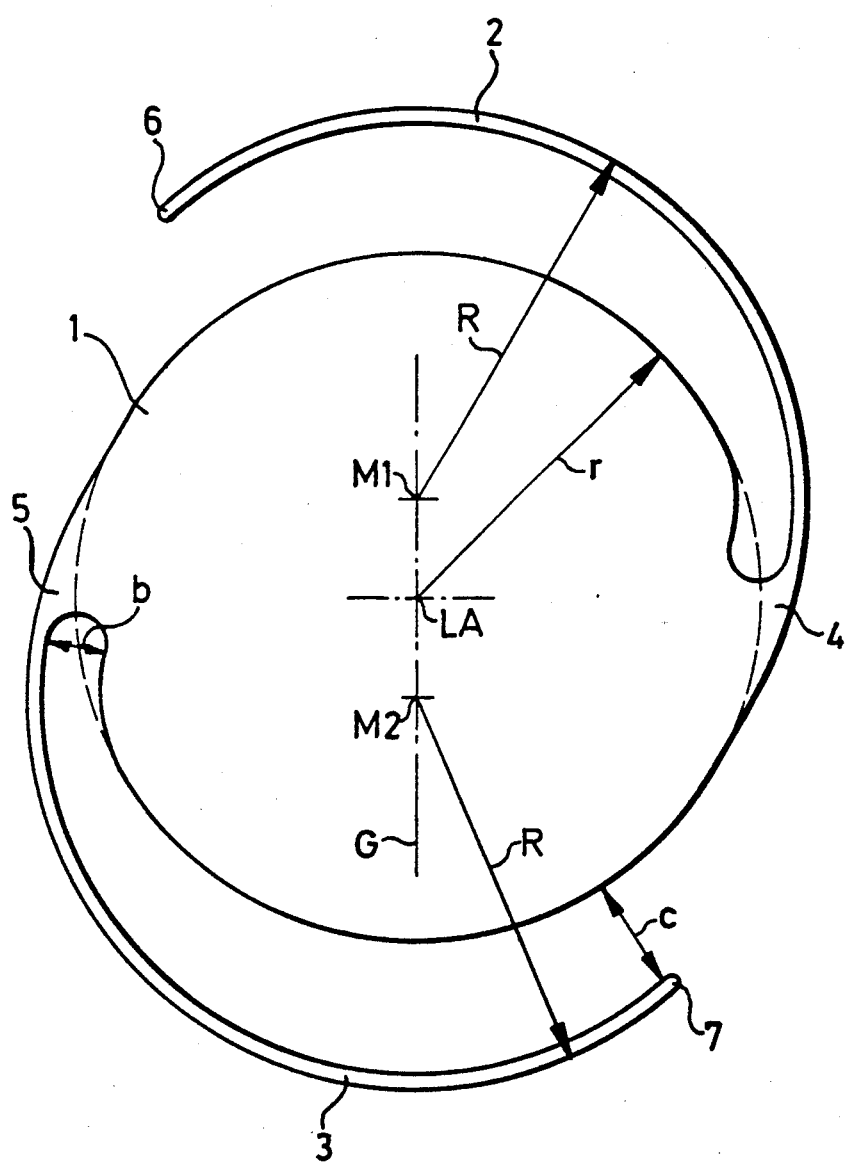
FIG. 1 shows a top view of the invention embodiment.
Figure 2:
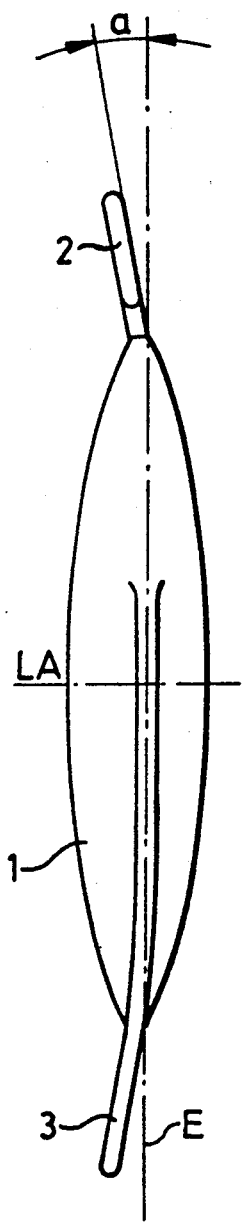
FIG. 2 shows a side view of the embodiment depicted in FIG. 1.

The embodiment of an intraocular posterior chamber lens depicted in FIGS. 1 and 2 has as its optical part a circular lens body 1. In the embodiment shown, the lens body 1 has a biconvex design and a relatively large thickness, which corresponds to a vertex refraction value on the order of 25.00 dpt. Naturally it is also possible to give the lens body 1 a thinner design for lower vertex refraction values, e.g. 10.0 dpt. The diameter of the lens body 1 is preferably 7.0 mm.

Any material compatible with the eye is suitable as a lens body material. A high polymer polymethyl acrylate is preferred. The lens body material can e.g. be provided with a UV absorber by means of polymerization.

Two fixation loops 2 and 3 are tangentially attached to the lens body 1 at attachment points 4, 5 which lie in diametrically opposite positions on the circumference of the lens body. These attachments points 4 and 5, which represent extensions from the circular shape (cross-hatched line in FIG. 1) of the lens body 1, are symmetrically positioned relative to the straight line G, which runs through the lens body axis LA and through two centers M1 and M2. The centers M1 and M2 are the centers of semicircles along which the two fixation loops 2 and 3 run. The outer circumference of these fixation loop semicircles each lie on circles of the same radius R (about 4 mm) around centers M1 and M2. The two centers M1 and M2 lie at equal distances from the axis LA of the lens body (about 1 mm). The circumference of the lens body 1 rests on a circle around lens body axis LA, with a radius r ($r=3.5$ mm in the depicted embodiment). The two outermost semicircular segments of fixation loops 2 and 3, relative to the lens body axis LA, lie on a circle whose center is located on lens body axis LA, which circle has a diameter of about 9.5 mm to 11.5 mm. The preferred diameter is 10.0 mm. In the embodiment the filament thickness is about 1.5 mm.

The distance separating the fixation loop 2 or 3 from the circumferential portion of the lens body 1 in the area of the attachment points 4 or 5 is smaller than the distance separating the loose end 6 or 7 of the fixation loop 2 or 3 from the corresponding circumferential area of the lens body 1. The distance b separating the fixation loop in the area of the attachment point 4 or 5 is about 0.4 mm in the embodiment and the distance c in the area of the loose end 6 or 7 is about 1.1 mm.

As can also be seen in FIG. 1, the lens body 1 diverges somewhat from circular shape in the area of the attachment points 4 and 5 and there displays slight recesses, which do not impede the optical functioning of the lens body. During implantation of the lens in the capuslar sack these recesses assure that, in conjunction with the flexible design of the two fixation loops 2 and 3, the two fixation loops 2 and 3 can be bent in the direction of lens body axis LA to conform with the diameter of the lens body 1, thereby considerably reducing the overall diameter of the intraocular lens during implantation. After insertion of the lens in the capsular sack, the fixation loops 2 and 3 expand and rest in the equatorial area of the capsular sack without causing strain, since their outer circumferences are designed to accomodate the equatorial area of the capsular sack.

As can be seen in FIG. 2, the fixation loops 2 and 3 are angled forward at an acute angle relative to plane E on which the circular circumference of the lens body 1 rests, i.e. in implanted condition they are angled toward the cornea of the eye. This acute angle is preferably 10°. This feature also helps assure a successful fixation, one which particularly guards against displacement in the forward direction.

I claim:

1. An intraocular posterior chamber lens for implantation in a human eye comprising a substantially circular biconvex optical lens body having a central axis and a haptic in the form of two elastic fixation loops for fixing the lens in the eye, each fixation loop being integral with the lens body and comprising a single limb extending substantially in a semi-circle from a junction point on the circumference of the lens body to a free end of the limb, the junction points of the respective limbs being positioned symmetrically on opposite sides of an imaginary straight line passing through said axis and the limbs extending from their respective junction points to their respective free ends in the same circumferential direction over the entire length of each limb, the limbs having respective centers located on said line at equal distances from and on opposite sides of said axis, each limb having an outer circumference extending from the respective junction point to the respective free end, the circumference configured for lying substantially in its entirety on a circle corresponding to the equator of the capsular sack of the eye when the lens is implanted.

2. A lens as defined in claim 1 wherein the lens body circumference lies in a plane and the fixation loops extend at an acute forward angle to said plane containing the lens body both on one side of said plane.

3. A lens as defined in claim 2 wherein said angle is about 10 degrees.

4. A lens as defined in claim 1 wherein said free ends of the respective limbs are separated by a distance of about 9.5 to 10.0 mm.

5. A lens as defined in claim 1 wherein the lens body has a diameter of about 7.0 mm.

6. A lens as defined in claim 1 wherein the lens body is made up of high polymer polymethyl acrylate.

7. A lens as defined in claim 1 made from a material which includes a UV absorber.

8. A lens as defined in claim 1 wherein the fixation loops are dimensioned for flexing to a configuration in which the entire outer circumference of the lens lies on a circle having a diameter of about 10 mm.

* * * * *